(12) United States Patent
Kantor et al.

(10) Patent No.: US 12,171,619 B2
(45) Date of Patent: *Dec. 24, 2024

(54) VARIABLE INTRALUMINAL ULTRASOUND TRANSMIT PULSE GENERATION AND CONTROL DEVICES, SYSTEMS, AND METHODS

(71) Applicant: PHILIPS IMAGE GUIDED THERAPY CORPORATION, San Diego, CA (US)

(72) Inventors: Sherwood Kantor, Sacramento, CA (US); Sidney Rhodes, Rancho Cordova, CA (US); Shukui Zhao, Folsom, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,564

(22) Filed: Dec. 5, 2022

(65) Prior Publication Data

US 2023/0095888 A1    Mar. 30, 2023

Related U.S. Application Data

(63) Continuation of application No. 16/354,116, filed on Mar. 14, 2019, now Pat. No. 11,517,291.

(Continued)

(51) Int. Cl.
*A61B 8/00* (2006.01)
*A61B 8/08* (2006.01)
*A61B 8/12* (2006.01)

(52) U.S. Cl.
CPC ............ *A61B 8/543* (2013.01); *A61B 8/12* (2013.01); *A61B 8/4438* (2013.01); *A61B 8/445* (2013.01);
(Continued)

(58) Field of Classification Search
None
See application file for complete search history.

(56) References Cited

U.S. PATENT DOCUMENTS

| 4,917,097 A | 4/1990 | Proudian |
| 5,368,037 A | 11/1994 | Eberle |

(Continued)

FOREIGN PATENT DOCUMENTS

JP    2010179018 A    8/2010

*Primary Examiner* — Shahdeep Mohammed

(57) ABSTRACT

Ultrasound image devices, systems, and methods are provided. In one embodiment, an intraluminal ultrasound imaging system includes a patient interface module (PIM) in communication with an intraluminal imaging device comprising an ultrasound imaging component, the PIM comprising a processing component configured to detect information associated with the intraluminal imaging device; and determine a waveform characteristic for ultrasound wave emissions at the ultrasound imaging component based on the detected information; and a trigger signal generation component in communication with the processing component and configured to generate a trigger signal based on the determined waveform characteristic to control the ultrasound wave emissions at the ultrasound imaging component.

14 Claims, 8 Drawing Sheets

Related U.S. Application Data

(60) Provisional application No. 62/643,453, filed on Mar. 15, 2018.

(52) U.S. Cl.
CPC ............ *A61B 8/4488* (2013.01); *A61B 8/461* (2013.01); *A61B 8/465* (2013.01); *A61B 8/488* (2013.01); *A61B 8/54* (2013.01)

(56) References Cited

U.S. PATENT DOCUMENTS

| | | | |
|---|---|---|---|
| 5,453,575 A | 9/1995 | O'Donnell | |
| 5,601,082 A | 2/1997 | Barlow | |
| 5,603,327 A | 2/1997 | Eberle | |
| 5,779,644 A | 7/1998 | Eberle | |
| 5,857,974 A | 1/1999 | Eberle | |
| 5,876,344 A | 3/1999 | Baker | |
| 5,921,931 A | 7/1999 | O'Donnell | |
| 5,938,615 A | 8/1999 | Eberle | |
| 6,033,357 A | 3/2000 | Ciezki | |
| 6,049,958 A | 4/2000 | Berle | |
| 6,085,410 A | 7/2000 | Toensing | |
| 6,123,673 A | 9/2000 | Eberle | |
| 6,165,128 A | 12/2000 | Cespedes | |
| 6,283,920 B1 | 9/2001 | Eberle | |
| 6,309,339 B1 | 10/2001 | Ciezki | |
| 6,381,350 B1 | 4/2002 | Klingensmith | |
| 6,457,365 B1 | 10/2002 | Stephens | |
| 6,712,767 B2 | 3/2004 | Hossack | |
| 6,725,081 B2 | 4/2004 | Ciezki | |
| 6,767,327 B1 | 7/2004 | Corl | |
| 6,776,763 B2 | 8/2004 | Nix | |
| 6,779,257 B2 | 8/2004 | Kiepen | |
| 6,785,415 B1 | 8/2004 | Taguchi | |
| 6,899,682 B2 | 5/2005 | Eberle | |
| 6,962,567 B2 | 11/2005 | Eberle | |
| 6,976,965 B2 | 12/2005 | Corl | |
| 7,097,620 B2 | 8/2006 | Corl | |
| 7,226,417 B1 | 6/2007 | Eberle | |
| 7,641,485 B2 | 1/2010 | Shibata | |
| 7,676,910 B2 | 3/2010 | Eberle | |
| 7,711,413 B2 | 5/2010 | Feldman | |
| 7,736,317 B2 | 6/2010 | Stephens | |
| 7,846,101 B2 | 12/2010 | Eberle | |
| 2007/0083111 A1 | 4/2007 | Hossack | |
| 2011/0015523 A1 | 1/2011 | Sabata | |
| 2012/0157843 A1 | 6/2012 | Lavin | |
| 2012/0179037 A1 | 7/2012 | Halmann | |
| 2013/0137978 A1 | 5/2013 | Lee | |
| 2013/0303910 A1* | 11/2013 | Hubbard | A61B 8/4461 600/443 |
| 2014/0187925 A1 | 7/2014 | Corl | |
| 2014/0187965 A1 | 7/2014 | Reiter | |
| 2014/0275844 A1 | 9/2014 | Hoseit | |
| 2014/0330126 A1 | 11/2014 | Kang | |
| 2014/0343434 A1* | 11/2014 | Elbert | A61B 8/4438 600/467 |
| 2016/0302772 A1 | 10/2016 | Cummins | |
| 2016/0317120 A1* | 11/2016 | Elbert | A61B 8/4461 |
| 2019/0110772 A1* | 4/2019 | Stigall | A61B 8/4416 |
| 2020/0333965 A1 | 10/2020 | Perez | |

* cited by examiner

VARIABLE INTRALUMINAL ULTRASOUND TRANSMIT PULSE GENERATION AND CONTROL DEVICES, SYSTEMS, AND METHODS

CROSS-REFERENCE TO RELATED APPLICATIONS

This Application is a continuation of U.S. application Ser. No. 16/354,116, filed Mar. 14, 2019, now U.S. Pat. No. 11,517,291, which claims priority to and the benefit of U.S. Provisional Application No. 62/643,453, filed Mar. 15, 2018, each of which is hereby incorporated by reference in its entirety.

TECHNICAL FIELD

The present disclosure relates generally to intraluminal imaging devices, in particular, to providing a patient interface module (PIM) that can control and vary intraluminal ultrasound transmit pulses in real time. For example, a PIM can be used with different types of intraluminal ultrasound imaging devices for different clinical imaging procedures. The PIM can automatically detect device information associated with an attached intraluminal ultrasound device and generate trigger signals to control ultrasound wave emissions at the intraluminal imaging device based on the device information.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed. IVUS imaging can provide detailed and accurate measurements of lumen and vessel sizes, plaque areas and volumes, and location of key anatomical landmarks. IVUS imaging allows physicians to evaluate the size of a lesion, select a treatment device (e.g., a stent) based on the evaluated lesion size, and subsequently evaluate the treatment success.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry an ultrasound imaging assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma.

Different clinical applications may require different types of IVUS catheters or different imaging modes. In other instances, different types of IVUS catheters or different imaging modes may be required during a clinical procedure. The different types of IVUS catheters and/or the different imaging modes may provide different imaging information through emitting ultrasound waves with different waveform characteristics. For example, different IVUS catheters may provide ultrasound wave emissions at different center frequencies. Different imaging modes (e.g., including imaging resolution, B-mode imaging, pulse-Doppler, continuous Doppler) may be used depending on the anatomy of interest and the required diagnostic information. The emissions of the ultrasound waves (e.g., ultrasound transmit pulses) at the transducers are driven by trigger signals. To generate ultrasound waves with different waveform characteristics, trigger signals with different waveform characteristics may be used.

In an IVUS imaging system, an ultrasound transmit pulse configuration is typically predetermined. Thus, the generation of the trigger signals is typically preconfigured for the system. As such, changes to the ultrasound transmit pulse configuration may require hardware and/or system changes.

SUMMARY

While existing IVUS imaging system have proved useful, there remains a need for improved systems and techniques for real-time system reconfigurations. Embodiments of the present disclosure provide a PIM that includes a detection component, a trigger signal generation component, and a controller. The detection component can detect an attachment of an IVUS catheter to the PIM. The IVUS catheter can include ultrasound transducers. The detection component can coordinate with the controller to identify device information (e.g., a serial number, a catheter type, an ultrasound attribute and/or a physiological sensing modality) associated with the IVUS catheter. The controller can obtain ultrasound waveform parameters specific to the IVUS catheter based on the identified device information. The controller can configure the trigger signal generation component to generate trigger signals for driving ultrasound wave emissions at the transducers based on the ultrasound waveform parameters. The controller can reconfigure the trigger signal generation component in real time based on an input from a user to change the ultrasound emission waveform characteristics at the transducers.

In one embodiment, an intraluminal ultrasound imaging system includes a patient interface module (PIM) in communication with an intraluminal imaging device comprising an ultrasound imaging component, the PIM comprising a processing component configured to detect information associated with the intraluminal imaging device; and determine a waveform characteristic for ultrasound wave emissions at the ultrasound imaging component based on the detected information; and a trigger signal generation component in communication with the processing component and configured to generate a trigger signal based on the determined waveform characteristic to control the ultrasound wave emissions at the ultrasound imaging component.

In some embodiments, the processing component is further configured to determine the waveform characteristic by determining at least one of a number of waveform pulses for the trigger signal, a periodicity of the waveform pulses, a duty cycle of the waveform pulses, a polarity of the waveform pulses, or an amplitude of the waveform pulses based on the detected information. In some embodiments, the PIM further comprises a field-programmable gate array (FPGA) including the processing component and the trigger signal generation component. In some embodiments, the FPGA further includes a plurality of registers, wherein the processing component is further configured to load values into the registers based on the determined at least one of a number of waveform pulses for the trigger signal, a periodicity of the waveform pulses, a duty cycle of the waveform pulses, a polarity of the waveform pulses, or an amplitude of the waveform pulses, and wherein the trigger signal generation component is further configured to generate the trigger signal based on the values in the registers. In some embodiments, wherein the ultrasound imaging component comprises an array of transducer elements, wherein the PIM further comprises a sequencing component in communication with the trigger signal generation component and configured to configure one or more timing sequences for one or more of the transducer elements in the array to produce the ultrasound wave emissions at the ultrasound imaging component. In some embodiments, the PIM further comprises a trigger signal application component configured to apply the trigger signal to the ultrasound imaging component based on the one or more timing sequences. In some embodiments, the PIM further comprises an interface coupled to the intraluminal imaging device; and a detection component coupled to the interface and the processing component, the detection component configured to detect an attachment of the intraluminal imaging device to the interface, and wherein the processing component is further configured to detect the information by reading the information from the intraluminal imaging device upon the detection. In some embodiments, the PIM is further in communication with a host system, and wherein the processing component is further configured to request a configuration for the intraluminal imaging device from the host system based on the detected information; receive the configuration from the host system in response to the request; and determine the waveform characteristic for the ultrasound wave emissions at the ultrasound imaging component based on the received configuration. In some embodiments, the PIM further comprises a memory configured to store a plurality of configurations associated with a plurality of different ultrasound imaging components comprising a plurality of different ultrasound attributes, wherein the processing component is further configured to select a configuration from the plurality of configurations based on the detected information associated the ultrasound imaging component; and determine the waveform characteristic for the ultrasound wave emissions at the ultrasound imaging component based on the selected configuration. In some embodiments, the PIM is further in communication with a user interface, wherein the processing component is further configured to receive a request from the user interface to modify a parameter associated with the ultrasound imaging component while the ultrasound imaging component is performing an imaging procedure; and determine an updated waveform characteristic for the ultrasound wave emissions at the ultrasound imaging component based on the modified parameter, and wherein the trigger signal generation component is further configured to generate an updated trigger signal based on the updated waveform characteristic; and apply the updated trigger signal to the ultrasound imaging component during the imaging procedure. In some embodiments, the modified parameter is associated with an imaging resolution, an imaging field-of-view, a B-mode imaging, and a Doppler-mode imaging. In some embodiments, wherein the information further includes at least one of a device type of the intraluminal imaging device, a serial number of the intraluminal imaging device, and one or more operational parameters of the intraluminal imaging device. In some embodiments, the intraluminal imaging device is an intravascular ultrasound (IVUS) catheter.

In one embodiment, a method of medical sensing includes detecting, by a patient interface module (PIM), information associated with an intraluminal imaging device in communication with the PIM, the intraluminal imaging device including an ultrasound imaging component; determining, by a processing component of the PIM, a waveform characteristic for ultrasound wave emissions at the ultrasound imaging component based on the detected information; generating, by a trigger signal generation component of the PIM, a trigger signal based on the determined waveform characteristic to control the ultrasound wave emissions at the ultrasound imaging component; and applying, by the trigger signal generation component, the trigger signal to the ultrasound imaging component.

In some embodiments, the determining includes determining at least one of a number of waveform pulses for the trigger signal, a periodicity of the waveform pulses, a duty cycle of the waveform pulses, a polarity of the pulses, or an amplitude of the waveform pulses based on the detected information. In some embodiments, the method further comprises configuring, by a sequencing component of the PIM, one or more timing sequences for one or more of transducer elements in a transducer array of the ultrasound imaging component to produce the ultrasound wave emissions at the ultrasound imaging component. In some embodiments, the method further comprises detecting, by a detection component of the PIM, an attachment of the intraluminal imaging device to the PIM, wherein the detecting includes reading the information from the intraluminal imaging device upon the detection. In some embodiments, the method further comprises requesting a configuration for the intraluminal imaging device from a host system based on the detected information; and receiving the configuration from the host system in response to the request, wherein the determining includes determining the waveform characteristic for the ultrasound wave emissions at the ultrasound imaging component based on the received configuration. In some embodiments, the method further comprises storing, at a memory of the PIM, a plurality of configurations associated with a plurality of different ultrasound imaging components comprising a plurality of different ultrasound attributes; and selecting a configuration from the plurality of configurations based on the detected information associated with the intraluminal imaging device, wherein the determining includes determining the waveform characteristic for the ultrasound wave emissions at the ultrasound imaging component based on the selected configuration. In some embodiments, the method further comprises receiving a request to modify a parameter associated with the waveform characteristic of the ultrasound wave emissions while the ultrasound imaging component is performing an imaging procedure; determining an updated waveform characteristic for the ultrasound wave emissions at the ultrasound imaging component based on the modified parameter; generating an updated trigger signal based on the updated waveform characteristic; and applying the updated trigger signal to the ultrasound imaging component during the imaging procedure.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
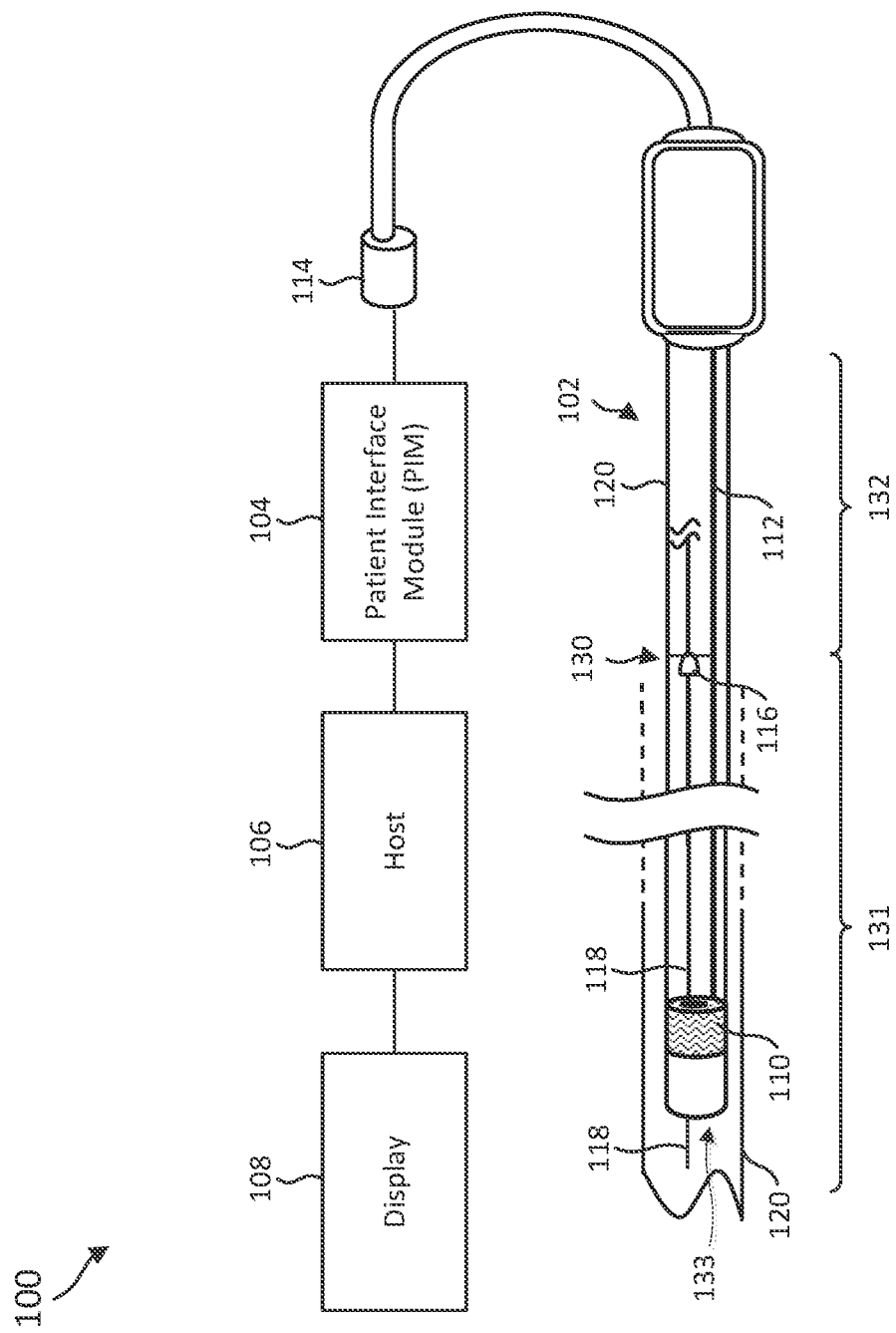
FIG. 1 is a schematic diagram of an intraluminal ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal ultrasound imaging system 100, according to aspects of the present disclosure. The system 100 may include an intraluminal imaging device 102, a patient interface module (PIM) 104, a host system 106, and a display 108. The intraluminal imaging device 102 may be a catheter, a guide wire, or a guide catheter. The intraluminal imaging device 102 can be referred to as an interventional device and/or a diagnostic device. In some instances, the intraluminal imaging device 102 can be a therapeutic device. The host system 106 may be a console, a computer, a laptop, a tablet, or a mobile device. The display 108 may be a monitor. In some embodiments, the display 108 may be an integrated component of the host system 106.

The intraluminal imaging device 102 may include a flexible elongate member sized and shaped for insertion into the vasculature of a patient. The flexible elongate member may include a distal portion 131 and a proximal portion 132. The intraluminal imaging device 102 may include an imaging component 110 mounted at the distal portion 131 near a distal end 133 of the intraluminal imaging device 102. The intraluminal imaging device 102 may be inserted into a body lumen or vessel 120 of the patient. For example, the intraluminal imaging device 102 can be inserted into a patient's vessel 120 to capture images of the structure of the vessel 120, measure the diameter and/or length of the vessel 120 to guide stent selection, and/or measure blood flow in the vessel 120. The vessel 120 may be any artery or vein within a vascular system of a patient, including cardiac vasculature, peripheral vasculature, neural vasculature, renal vasculature, and/or any other suitable anatomy/lumen inside the body. In some embodiments, the vessel 120 may be a venous vessel, a pulmonary vessel, a coronary vessel, or a peripheral vessel. For example, the device 102 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within vasculature or the heart, chambers or other parts of the heart, and/or other systems of the body. In addition to natural structures, the device 102 may be used to examine man-made structures such as, but without limitation, heart valves, stents, shunts, filters and other devices.

In an embodiment, the imaging component 110 may include ultrasound transducers configured to emit ultrasonic energy towards the vessel 120. The emission of the ultrasonic energy may be in the form of pulses. The ultrasonic energy is reflected by tissue structures and/or blood flows in the vessel 120 surrounding the imaging component 110. The reflected ultrasound echo signals are received by the ultrasound transducers in the imaging component 110. In some instances, the imaging component 110 may be configured for brightness-mode (B-mode) imaging to capture images of vessel structures or to measure vessel diameters and lengths for stent selection. In some other instances, the imaging component 110 may be configured for Doppler color flow imaging to provide blood flow measurements. In yet some other instances, the imaging component 110 may be configured to operate in a dual-mode to provide both B-mode imaging data and Doppler flow measurements.

In some embodiments, the ultrasound transducers in the imaging component are phased-array transducers, which may be configured to emit ultrasound energy at a frequency of about 10 megahertz (MHz) to about 20 MHz. In some other embodiments, the imaging component 110 may be alternatively configured to include a rotational transducer to provide similar functionalities. The PIM 104 transfers the received echo signals to the host system 106 where the ultrasound image is reconstructed and displayed on the display 108. For example, the strengths or the amplitudes of the echo responses may be converted to brightness or intensity levels for gray-scale image display.

The host system 106 can include a processor and a memory. The host system 106 can be operable to facilitate the features of the system 100 described herein. For example, the processor can execute computer readable instructions stored on the non-transitory tangible computer readable medium.

The PIM 104 facilitates communication of signals between the host system 106 and the intraluminal imaging device 102 to control the operation of the imaging component 110. This includes generating control signals to configure the imaging component 110, triggering transmitter circuits to cause the imaging component 110 to emit ultrasound waves, and transferring echo signals captured by the imaging component 110 to the host system 106. With regard to the echo signals, the PIM 104 forwards the received signals and, in some embodiments, performs preliminary signal processing prior to transmitting the signals to the host 106. In examples of such embodiments, the PIM 104 performs amplification, filtering, and/or aggregating of the data. In an embodiment, the PIM 104 also supplies high- and low-voltage direct current (DC) power to support operation of the circuitry within the imaging component 110. Mechanisms for triggering the transmitter circuits are described in greater detail herein.

In an embodiment, the host system 106 receives the echo data from the imaging component 110 and/or transmits controls to the imaging component 110 by way of the PIM 104. The host system 106 processes the echo data to reconstruct an image of the tissue structures in the vessel 120 surrounding imaging component 110. The host system 106 outputs image data such that an image of the vessel 120, such as a cross-sectional image of the vessel 120, is displayed on the display 108.

In some embodiments, the intraluminal imaging device 102 includes some features similar to traditional solid-state IVUS catheters, such as the EagleEye® Platinum, Eagle Eye® Platinum ST, Eagle Eye® Gold, and Visions® PV catheters available from Volcano Corporation and those disclosed in U.S. Pat. No. 7,846,101 hereby incorporated by reference in its entirety. For example, the intraluminal imaging device 102 further includes an electrical cable 112 extending along the longitudinal body of the intraluminal imaging device 102. The cable 112 is a transmission line bundle including a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 American wire gauge (AWG) wires. In an embodiment, the cable 112 can include a seven-conductor transmission line arrangement utilizing, e.g., 44 AWG wires. In some embodiments, 43 AWG wires can be used. In some other embodiments, the intraluminal imaging device 102 includes some features similar to traditional rotational IVUS catheters, such as the Revolution® catheter available from Volcano Corporation and those disclosed in U.S. Pat. Nos. 5,601,082 and 6,381,350, each of which is hereby incorporated by reference in its entirety. In some embodiments, the intraluminal imaging device 102 includes components or features similar or identical to those disclosed in U.S. Pat. Nos. 4,917,097, 5,368,037, 5,453,575, 5,603,327, 5,779,644, 5,857,974, 5,876,344, 5,921,931, 5,938,615, 6,049,958, 6,0854,109, 6, 123,673, 6,165, 128, 6,283,920, 6,309,339; 6,033,357, 6,457,365, 6,712,767, 6,725,081, 6,767,327, 6,776, 763, 6,779,257, 6,7854, 157, 6,899,682, 6,962,567, 6,976,965, 7,097,620, 7,226,417, 7,641,4854, 7,676,910, 7,711,413, and 7,736,317, each of which is hereby incorporated by reference in its entirety.

The cable 112 terminates in a PIM connector 114 at a proximal end of the intraluminal imaging device 102. The PIM connector 114 electrically couples the cable 112 to the PIM 104 and physically couples the intraluminal imaging device 102 to the PIM 104. In an embodiment, the intraluminal imaging device 102 further includes a guide wire exit port 116 disposed near a junction 130 at which the distal portion 131 is coupled to the proximal portion 132. Accordingly, in some instances the intraluminal imaging device 102 is a rapid-exchange catheter. The guide wire exit port 116 allows a guide wire 118 to be inserted towards the distal end 133 in order to direct the intraluminal imaging device 102 through the vessel 120.

Different clinical or imaging applications may require the use of different types of intraluminal imaging devices 102, which may have different dimensions and/or different imaging capabilities. For example, imaging of peripheral vessels, imaging of coronary vessels, measurements of blood flow, and evaluations of vascular morphology in blood vessels may each require a particular type of intraluminal imaging device 102.

In addition, different imaging modes may be required to obtain different type of diagnostic information (e.g., B-mode data and color Doppler flow data). Different ultrasound center frequencies may be used to compromise signal penetration depths and image resolution. For example, the imaging component 110 may be configured to emit ultrasound waves at a higher center frequency to provide a higher imaging resolution, trading off penetration depth. Conversely, the imaging component 110 may be configured to emit ultrasound waves at a lower center frequency to provide a deeper penetration, trading off imaging resolution.

Further, different ultrasound pulse durations may be used. For example, the imaging component 110 may be configured to emit ultrasound pulses with a shorter duration, but at a higher signal energy level. For example, higher-energy ultrasound waves can be used during color flow imaging to provide a better view of blood vessel boundaries. Alternatively, higher-energy ultrasound waves can be used to provide a larger field-of-view during peripheral imaging due to the larger peripheral vessel sizes, for example, when capturing an image of an aorta artery during abdominal imaging or an iliac artery during limb imaging.

Thus, different imaging results or diagnostic information may be achieved with different ultrasound waveform shapes or waveform parameters, such as center frequency, a bandwidth, amplitude, pulse duration, duty cycle, and/or the number of pulses or cycles. In an embodiment, the PIM 104 may provide variable controls of trigger signals such that ultrasound wave emissions at the intraluminal imaging device 102 may dynamically adapt to the intraluminal imaging device 102 under use, the desired clinical application, and/or imaging parameter modifications during a clinical procedure, as described in greater detail herein.

Figure 2:
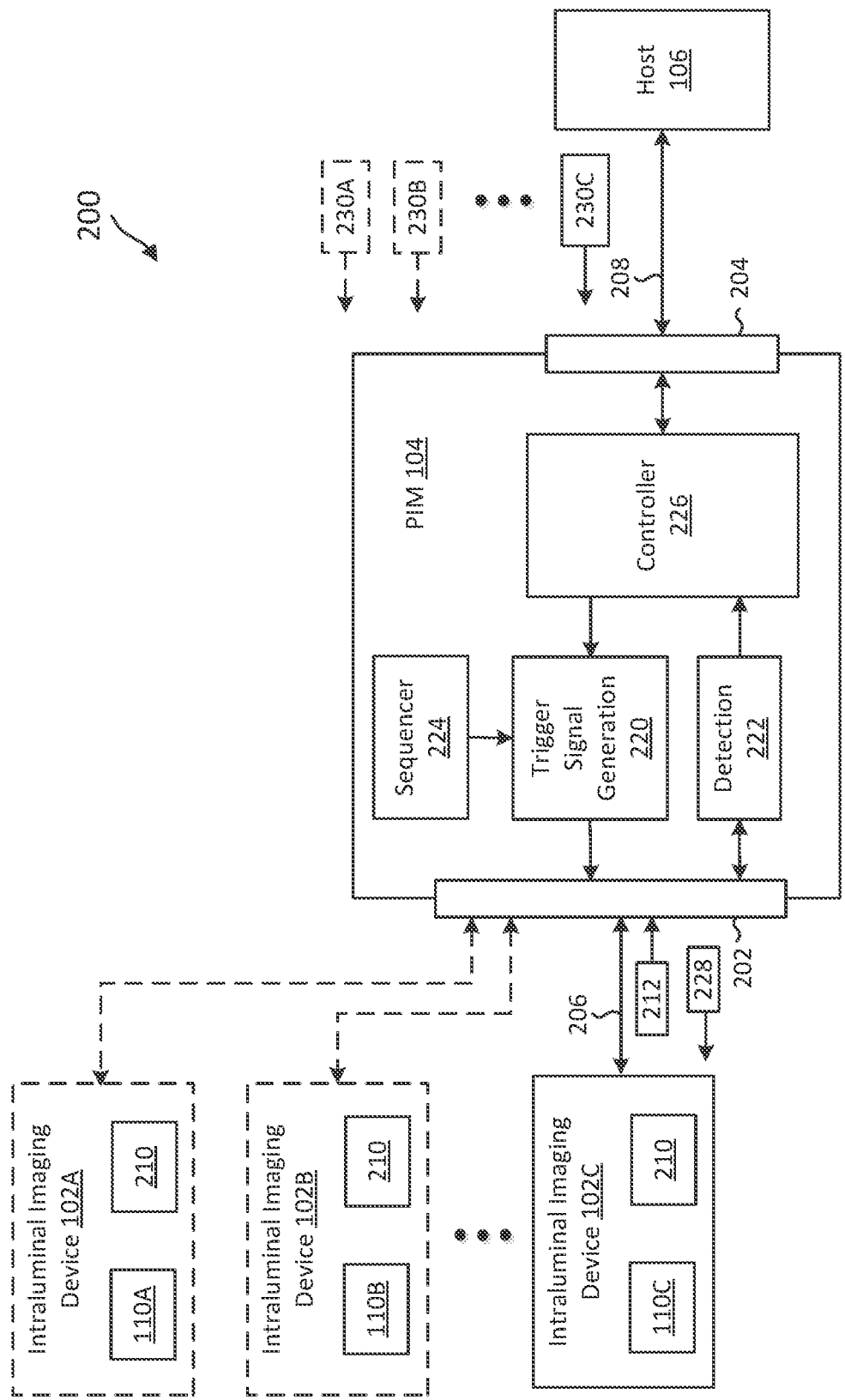
FIG. 2 is a schematic diagram illustrating a system configuration for an intraluminal ultrasound imaging system, according to aspects of the present disclosure.

FIG. 2 is a schematic diagram illustrating a system configuration 200 for the intraluminal ultrasound imaging system 100, according to aspects of the present disclosure.

FIG. 2 provides a more detailed view of the internal components of the PIM 104 and interactions among the PIM 104, the host 106, and the intraluminal imaging device 102 in communication with the PIM 104. At a high level, upon an attachment of the intraluminal imaging device 102 to the PIM 104. The PIM 104 can detect and identify device information 212 associated with an intraluminal imaging device 102. The PIM 104 can request a parameter configuration 230 (e.g., parameters for a desired ultrasound waveform) specific to the attached intraluminal imaging device 102 from the host 106 based on the identified device information 212. The PIM 104 can generate trigger signals 228 based on the received parameter configuration 230. The trigger signals 228 can trigger or drive the imaging component 110 of the attached intraluminal imaging device 102 to emit ultrasound waves with the desired waveform. The trigger signals 228 may be electrical signals. In some instances, the trigger signals 228 may be high-voltage signals. As shown, the PIM 104 includes a device interface 202, a trigger signal generation component 220, a detection component 222, a sequencer 224, a controller 226, and a host interface 204.

The device interface 202 may include a common intraluminal imaging device interface connector suitable for coupling with various different intraluminal imaging devices 102. The intraluminal imaging devices are shown as 102A, 102B, and 102C. As an example, the intraluminal imaging device 102A may be a rotational IVUS catheter including an imaging component 110A with a single ultrasound transducer element. The intraluminal imaging device 102B may be a solid-state IVUS catheter, for example, suitable for coronary imaging. The intraluminal imaging device 102C may include an imaging component 110C with phased-array ultrasound transducers. The intraluminal imaging device 102C may be another solid-state IVUS catheter, for example, suitable for peripheral imaging. The intraluminal imaging device 102C may include an imaging component 110C with phased-array ultrasound transducers.

The different intraluminal imaging devices 102A, 102B, and 102C may have different dimensions, different imaging capabilities (e.g., ultrasound center frequencies), and/or different sets of control parameters. The imaging components 110A, 110B, and 110C may require different trigger signals for ultrasound wave emissions. For example, the imaging components 110A, 110B, and 110C may be designed to emit ultrasound waves with different center frequencies. Each intraluminal imaging device 102 may include a memory 210. The memory 210 may be a non-volatile memory, such as an electrically erasable programmable read-only memory (EEPROM), configured to store device information, such as a serial number, a device identification number, a catheter type, and other operational parameters (e.g., ultrasound attributes and/or a physiological sensing modality) related to a corresponding ultrasound imaging component 110.

The host interface 204 may include hardware components and/or software components configured to communicate with the host 106 via a link 208. In some instances, the communication link 208 may be a wired connection, such as an Ethernet link, a universal serial bus (USB) link, or any suitable wired communication link. In other instances, the link 208 may be a wireless link, such as an Institute of Electrical and Electronics Engineers (IEEE) 802.11 (WiFi) link, a Bluetooth link, a Zigbee link, or an ultra-wideband (UWB) link.

The detection component 222 is coupled to the device interface 202 and the controller 226. The detection component 222 may include logics configured to detect an attachment of an intraluminal imaging device 102 and notify the controller 226 of the detection. As an example, a user or a clinician may select the intraluminal imaging device 102C for a particular clinical application and connect the intraluminal imaging device 102C to the device interface 202 at the PIM 104 as shown by the solid link 206. The detection component 222 may notified the controller 226 of the detected attachment.

The controller 226 is coupled to the trigger signal generation component 220, the sequencer 224, and the host interface 204. The controller 226 may include hardware components and/or software components. The controller 226 is configured to receive a device detection or attachment notification from the detection component 222 and read the device information 212 from the attached intraluminal imaging device 102 (e.g., from the memory 210 of the intraluminal imaging device 102C). The controller 226 may request a parameter configuration 230 from the host 106 based on the identified device information 212. The parameter configuration 230 may include parameters for controlling and/or configuring the attached intraluminal imaging device 102. For example, when the controller 226 identifies that the intraluminal imaging device 102A is in communication with the PIM 104, the controller 226 may request the parameter configuration 230A from the host 106. Alternatively, when the controller 226 identifies that the intraluminal imaging device 102B is in communication with the PIM 104, the controller 226 may request the parameter configuration 230B from the host 106. Yet alternatively, when the controller 226 identifies that the intraluminal imaging device 102C is in communication with the PIM 104, the controller 226 may request the parameter configuration 230C from the host 106.

Each of the parameter configurations 230A, 230B, and 230C may include ultrasound waveform parameters for a corresponding intraluminal imaging device 102. Examples of ultrasound waveform parameters may include one or more operating ultrasound center frequencies, an ultrasound signal bandwidth, an ultrasound pulse duration, a number of signal zones in a pulse, a pulse amplitude, a pulse polarity, a pulse duty cycle, a number of pulses, or any other suitable parameters that describe a waveform shape or a waveform characteristic. The controller 226 may configure the trigger signal generation component 220 based on the received parameter configuration 230. In some embodiments, the controller 226 may determine additional waveform parameters based on the received parameter configuration 230 and further configure the trigger signal generation component 220 based on the determined waveform parameters.

The trigger signal generation component 220 is coupled to the device interface 202 and in communication with the attached intraluminal imaging device 102 (e.g., the intraluminal imaging device 102C). The trigger signal generation component 220 may include software components and/or hardware components (e.g., logics and circuitry) configured to generate a trigger signal 228 according to the configuration applied by the controller 226. The trigger signal 228 is applied to the imaging component 110 (e.g., the imaging component 110C) of the attached intraluminal imaging device 102. The trigger signal 228 may initiate or trigger the imaging component 110 to emit ultrasound waves.

The sequencer 224 is coupled to the trigger signal generation component 220. The sequencer 224 may include software components and/or hardware components configured to determine a sequence order and timing for ultrasound transducer elements (e.g., at the imaging component 110C) to transmit and/or receive, for example, to provide synthetic aperture ultrasound imaging, as described in greater detail herein.

As an example, when the intraluminal imaging device 102A is connected to the PIM 104, the controller 226 can automatically identify that the intraluminal imaging device 102A is in communication with the PIM 104. The controller 226 can obtain the parameter configuration 230A associated with the intraluminal imaging device 102A and dynamically configure the trigger signal generation component 220 to generate a trigger signal 228 including a waveform specific to ultrasound attributes of the imaging component 110A.

Alternatively, when the intraluminal imaging device 102B is connected to the PIM 104, the controller 226 can automatically identify that the intraluminal imaging device 102B is in communication with the PIM 104. The controller 226 can obtain the parameter configuration 230B associated with the intraluminal imaging device 102B and dynamically configure the trigger signal generation component 220 to generate a trigger signal 228 including a waveform specific to ultrasound attributes of the imaging component 110B.

Figure 3:
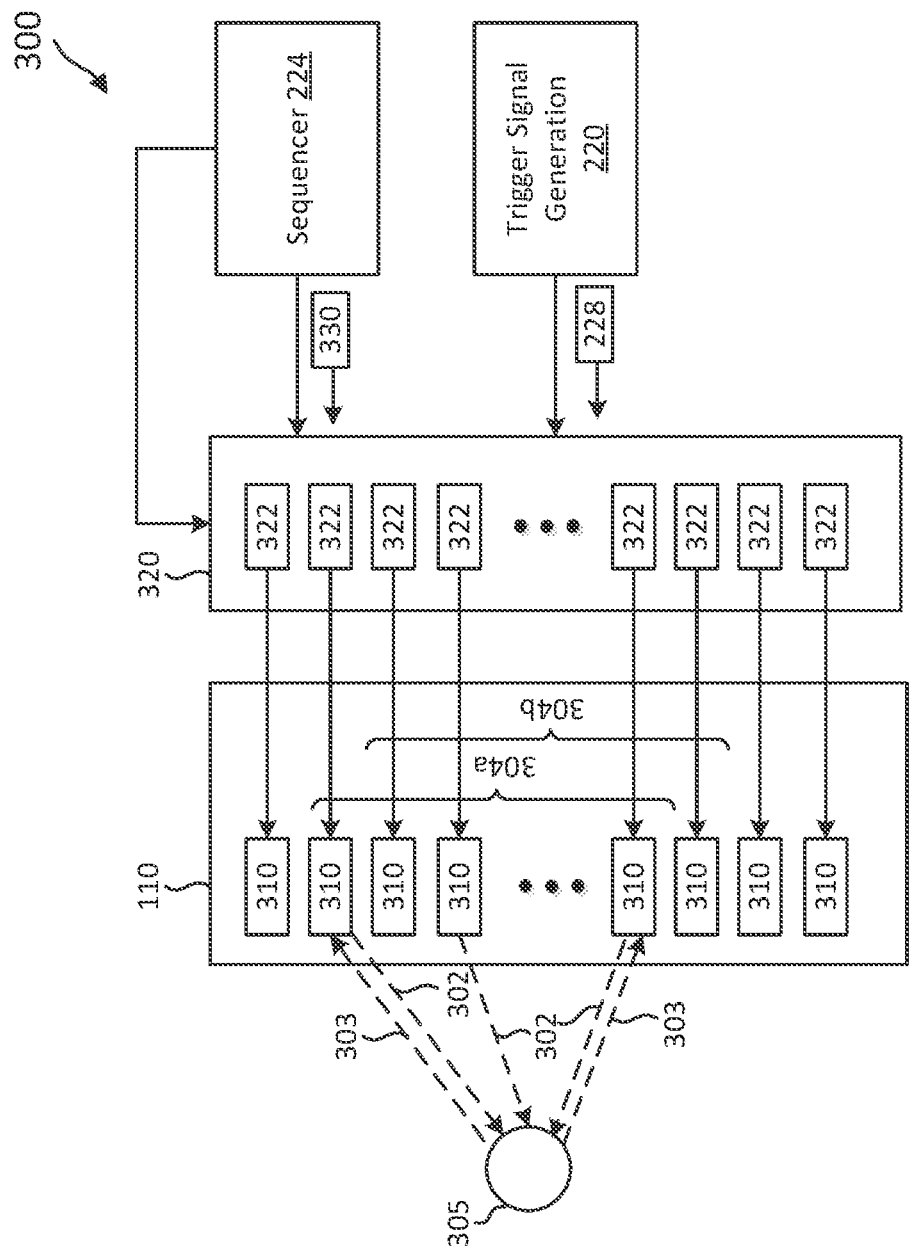
FIG. 3 is a schematic diagram illustrating an ultrasound imaging configuration, according to aspects of the present disclosure.

FIG. 3 is a schematic diagram illustrating an ultrasound imaging configuration 300, according to aspects of the present disclosure. The configuration 300 provides a more detailed view of the interactions between the sequencer 224 and the trigger signal generation component 220 for providing synthetic aperture ultrasound imaging. The configuration 300 includes a multiplexer 320 coupled to the imaging component 110, the sequencer 224, and the trigger signal generation component 220. The imaging component 110 may correspond to an imaging component 110C of the intraluminal imaging device 102C attached to the PIM 104 shown in FIG. 2. The imaging component 110C may include an array of ultrasound transducers 310.

The multiplexer 320 may include a plurality of transmit switching circuitries 322. Each transmit switching circuitry 322 may be coupled to one of the transducers 310. Each transmit switching circuitry 322 may include a driver that can activate ultrasound wave emissions at transducers 310 and a switch that can gate or allow an electrical signal (e.g., a trigger signal 228) to pass through to a corresponding transducer 310.

As described above, the sequencer 224 controls the timing and the sequence of activations at the transducers 310 (e.g., for emitting ultrasound waves) and the trigger signal generation component 220 generates trigger signals to activate the transducers 310 based on waveform parameters provided by the controller 226. The transmit switching circuitries 322 in the multiplexer 320 may receive trigger signals 228 from the trigger signal generation component 220 and send the trigger signals 228 through to the transducers 310 according to the timing and sequence provided by the sequencer 224. For example, the sequencer 224 may provide a timing sequence 330 indicating a sequence (e.g., including an order and timing) for firing a set of transducers 310.

In some embodiments, the transducers 310 may be grouped into apertures 304, including apertures 304a and 304b. In some embodiments, each transducer 310 may be part of one or more apertures 304. Each aperture 304 may include any suitable number of transducers 310. The sequencer 224 may activate one or more transducers 310 in an aperture 304 to emit ultrasound waves 302. The ultrasound waves 302 may be emitted towards a target anatomical structure 305 (e.g., a blood vessel). While not shown in FIG. 3, the configuration 300 may further include receive switching circuitries coupled to the transducer so that the sequencer 224 may also activate one or more transducers 310 in the aperture 304 to receive echo signals 303 reflected back from the structure 305. The received echo signals 303 may create an A-line in an image representing the structure 305.

While the multiplexer 320 is illustrated with a separate transmit switching circuitry 322 for each transducer 310, the transmit switching circuitries 322 can be configured in any suitable configuration, for example, some transducers 310 may be coupled to the same transmit switching circuitry 322. In addition, in some embodiments, the sequencer 224 may be coupled to the trigger signal generation component 220. The sequencer 224 can coordinate with the trigger signal generation component 220 to control the triggering of transmit pulses at the imaging component 110.

Figure 4:
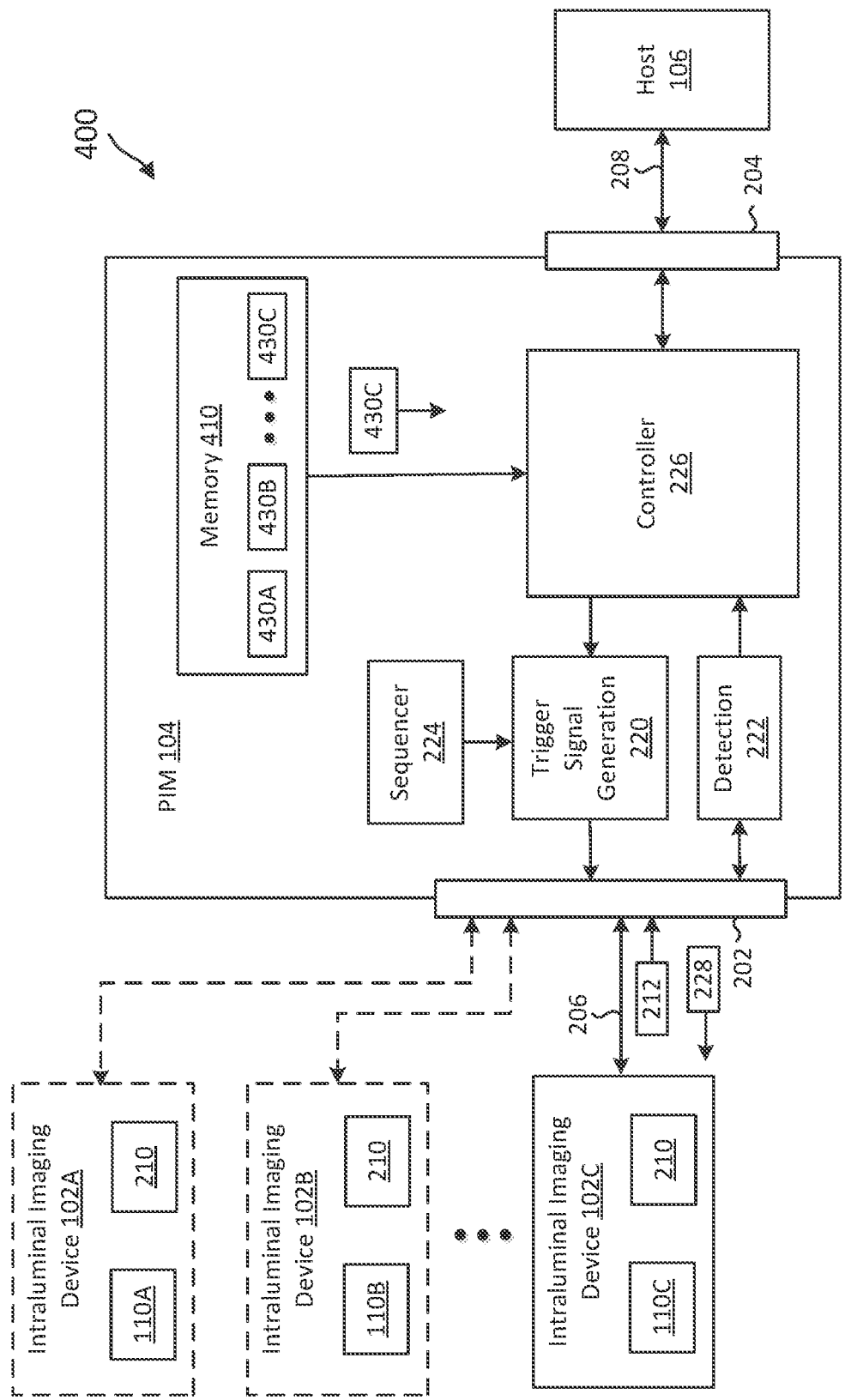
FIG. 4 is a schematic diagram illustrating a system configuration for an intraluminal ultrasound imaging system, according to aspects of the present disclosure.

FIG. 4 is a schematic diagram illustrating a system configuration 400 for the intraluminal ultrasound imaging system 100, according to aspects of the present disclosure. The system configuration 400 may be substantially similar to the system configuration 200. For example, the PIM 104 can detect an attachment of an intraluminal imaging device 102C, identify device information 212 of the attached intraluminal imaging device 102C, and generate trigger signals 228 for the intraluminal imaging device 102 based on the identified device information 212. However, in the system configuration 400, the PIM 104 may include a memory 410 coupled to the controller 226. The memory 410 may be a non-volatile memory, such as an EEPROM, configured to store multiple parameter configurations 430. The parameter configurations 430 may be device-specific and may be substantially similar to the parameter configurations 230. For example, the parameter configurations 430A, 430B, and 430C may be used for configuring the intraluminal imaging devices 102A, 102B, and 102C, respectively. Thus, upon identifying the device information 212 of the attached intraluminal imaging device 102C, the controller 226 may select a configuration from the parameter configurations 430 stored in the memory 410 based on the identified device information 212 instead of requesting from a host 106 as in the system configuration 200.

Figure 5:
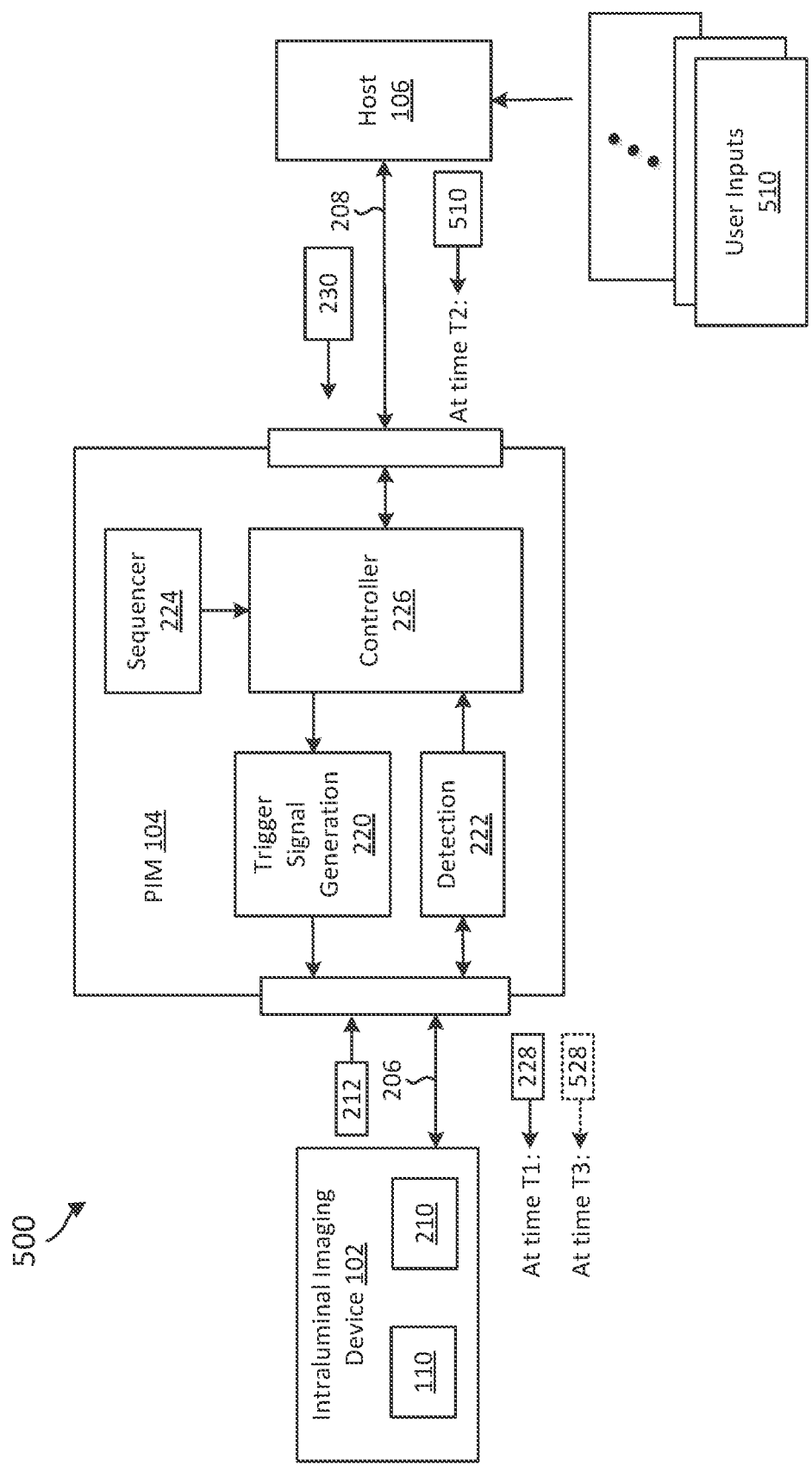
FIG. 5 is a schematic diagram illustrating a system configuration for an intraluminal ultrasound imaging system, according to aspects of the present disclosure.

FIG. 5 is a schematic diagram illustrating a system configuration 500 for the intraluminal ultrasound imaging system 100, according to aspects of the present disclosure. The system configuration 500 may be substantially similar to the system configuration 200. For example, the PIM 104 can detect an attachment of an intraluminal imaging device 102, identify device information 212 of the attached intraluminal imaging device 102, and generate trigger signals 228 for the intraluminal imaging device 102 based on the identified device information 212. However, in the system configuration 500, the host 106 can receive user inputs 510 during a clinical imaging clinical procedure while the intraluminal imaging device 102 is in use and the PIM 104 can dynamically reconfigure the waveform of the ultrasound wave emissions at the imaging component 110 based on the user inputs 510 in real-time.

For example, a clinician performing a clinical procedure may decide to adjust or modify ultrasound imaging parameters, such as the ultrasound center frequency, the pulse duration, the duty cycle, the polarity of the pulses, the signal energy level, and/or the number of cycles. The clinician may input the desired adjustment or modification as a user input 510 to the host 106, for example, via a graphical user interface (GUI) on a console, a mouse, a keyboard, a touch screen, or the like. The host 106 may send the user input 510 to the PIM 104 via the link 208. The controller 226 may receive the user input 510 and reconfigure the trigger signal generation component 220 based on the user input 510. In some instances, the user input 510 may include a waveform parameter for controlling ultrasound wave emissions at the imaging component 110. In other instances, the controller 226 may determine a waveform parameter for controlling ultrasound wave emissions at the imaging component 110 based on the user input 510.

As an example, at the beginning of the procedure (e.g., at time T1), the controller 226 configures the trigger signal generation component 220 to generate a trigger signal 228 based on a parameter configuration 230 received from the host 106. Subsequently, at time T2, the user enters a user input 510 to modify a waveform parameter. In response, the controller 226 reconfigures the trigger signal generation component 220 to generate an updated trigger signal 528 based on the modified parameter received from the user input 510. At time T3, the updated trigger signal 528 (shown as dotted box) is applied to the imaging component 110. The updated trigger signal can be applied based on a timing provided by the sequencer 224, for example, for a subsequent activation.

As can be seen, the system configuration 500 allows a user to modify an imaging configuration or transmit ultrasound pulses without changing any hardware and/or system components (e.g., the PIM 104) or rebooting the system 100.

Figure 6:
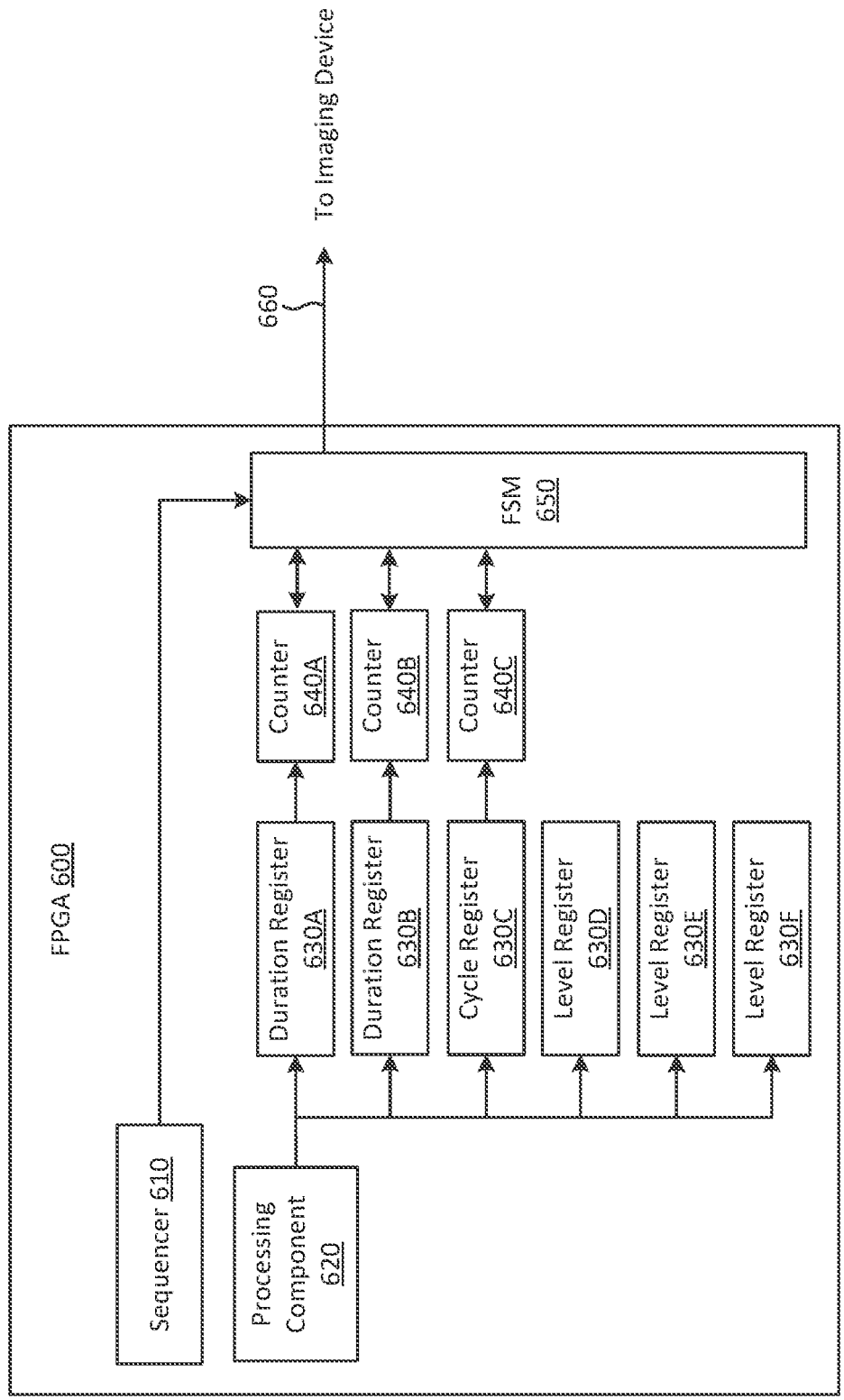
FIG. 6 is a schematic diagram illustrating a field-programmable gate array (FPGA) implementation for generation and control of variable ultrasound transmit pulses, according to aspects of the present disclosure.
Figure 7:
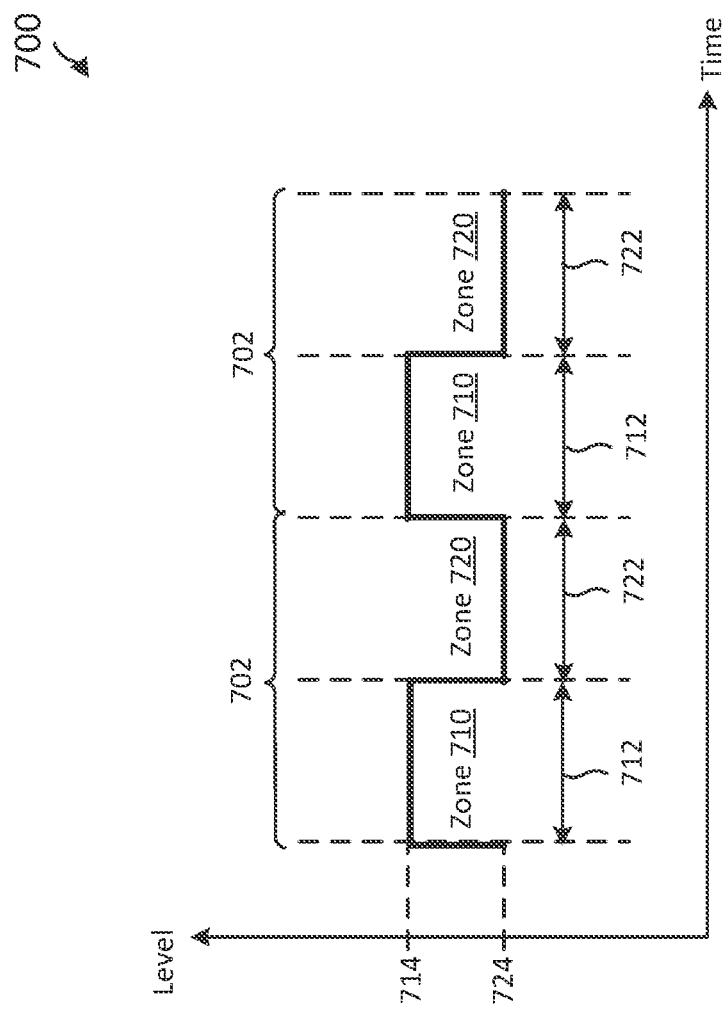
FIG. 7 is a graph illustrating a trigger signal for controlling ultrasound wave emissions, according to aspects of the present disclosure.

FIG. 6 is a schematic diagram illustrating an FPGA 600 implementation for generation and control of variable ultrasound transmit pulses, according to aspects of the present disclosure. For example, the FPGA 600 can be located within the PIM 104. FIG. 7 is a graph illustrating a trigger signal 700 for controlling ultrasound wave emissions, according to aspects of the present disclosure. In FIG. 7, the x-axis represents time in some constant units and the y-axis represents signal voltage levels in some constant units.

The FPGA 600 may include a plurality of configurable logic blocks connected by programmable interconnects. As shown, the FPGA 600 is configured to implement a sequencer 610, a processing component 620, a plurality of registers 630, a plurality of counters 640, and a finite state machine (FSM) 650.

The sequencer 610 may be substantially similar to the sequencer 224. The sequencer 610 is configured to provide a timing sequence for firing or triggering any array of transducer elements (e.g., the transducers 310) in an imaging component 110, for example, for synthetic aperture ultrasound imaging as described above in the ultrasound imaging configuration 300 with respect to FIG. 3.

The processing component 620 may be a programmable controller, such as a microcontroller. A software or firmware may be executed on the processing component 620 to provide similar ultrasound transmit pulse controls as the controller 226. For example, the processing component 620 can obtain a parameter configuration (e.g., the parameter configurations 230 and 430) from a host (e.g., the host 106) or selected from configurations stored in a memory (e.g., the memory 410) included in the FPGA 600. The configuration can include parameters that control the waveform shape of an ultrasound wave emission.

The registers 630 may be accessible (e.g., for reading and writing) by the processing component 620. For example, the processing component can load parameter values into the registers 630. Each counter 640 may perform a counting function, which may count-up or count-down, based on a corresponding register 630. The FSM 650 may access the counters 640 and the registers 630. The FSM 650 may generate a trigger signal or a sequence of pulses at an output line 660 based on values in the registers 630 and may use the counters 640 for state transitions, as described in greater detail herein.

In some embodiments, while not shown, the FSM 650 may be coupled to each counter 640 via multiple signal lines, for example, a load line, a decrement line, and a value line. The FSM 650 may load a value into a counter 640 via a corresponding load line. The FSM 650 can trigger a decrement of the value in a counter 640 via a corresponding decrement line. The FSM 650 may read or retrieve the value from counter 640 via the value line.

As an example, the FPGA 600 is configured to generate the trigger signal 700 (e.g., the trigger signals 228 and 528). FIG. 7 illustrates two trigger pulses 702 each with two signal zones 710 and 720 for purposes of simplicity of discussion, though it will be recognized that embodiments of the present disclosure may scale to include any suitable number of pulses 702 (e.g., 5, 10, 12, or 20) in the trigger signal 700. The duration 712 and the level 714 of the zone 710, the duration 722 and the level 724 of the zone 720, and the number of cycles or pulses 702 are configurable or programmable and may be varied to provide different ultrasound wave emission with different waveform shapes. The configuration may include values for the durations 712 and 722, the levels 714 and 724, and the number of cycles or pulses 702. For example, the center frequency of an ultrasound wave may be varied by varying the durations 712 and 722. The signal energy level of an ultrasound wave may be varied by varying the levels 714 and 724.

For example, the processing component 620 can load values of the duration 712 and the level 714 of the zone 710 into a duration register 630A and a level register 630D, respectively. The processing component 620 can load values of the duration 722 and the level 724 of the zone 720 into a duration register 630B and a level register 630E, respectively. The processing component 620 can load a cycle register 630C with the number of cycles or pulses 702. In some instances, the processing component 620 can load a default level value into a level register 630F.

The bit-widths of the duration registers 630 may vary depending on the embodiments. In some embodiments, the duration registers 630A and 630B each may have a bit-width of about 12 bits to hold a duration value between about 0 to about 4095. The cycle register 630C may have a bit-width of about 4 bits to hold a cycle number value between about 0 and 15. The level registers 630D, 630E, and 630F each may have a bit-width of about 1 bit to hold an assertion level value of 0 (e.g., a low level) or 1 (e.g., a high level).

The FSM 650 may generate the trigger signal 700 based on the values in the registers 630 and the counters 640. As an example, the FSM 650 may load the value in the cycle register 630C into the counter 640C (e.g., via a corresponding load line) and the value in duration register 630A into the counter 640A. The FSM 650 may generate the zone 710 by holding the trigger signal 700 at a signal level (e.g., the signal level 714) based on the value in the level register 630D. The counter 640A may count down.

When the counter 640A counts to 0, the FSM 650 may transition to generate the zone 720. The FSM 650 may load the counter 640B with the value in duration register 630B. The FSM 650 may transition the signal to a next signal level (e.g., the signal level 724) based on the value in the level register 630E. Similar to the counter 640A, the counter 640B may count down.

When the counter 640B counts to 0, the FSM 650 may decrement the counter 640C (e.g., via a corresponding decrement line). When the value in the counter 640C is greater than 0, the FSM 650 may repeat the generation of the zones 710 and 720 as described above to produce a next pulse 702. For example, the FSM 650 may read the value in the counter 640C (e.g., via a corresponding value line) to determine whether the value is greater than 0 after the decrement.

Figure 8:
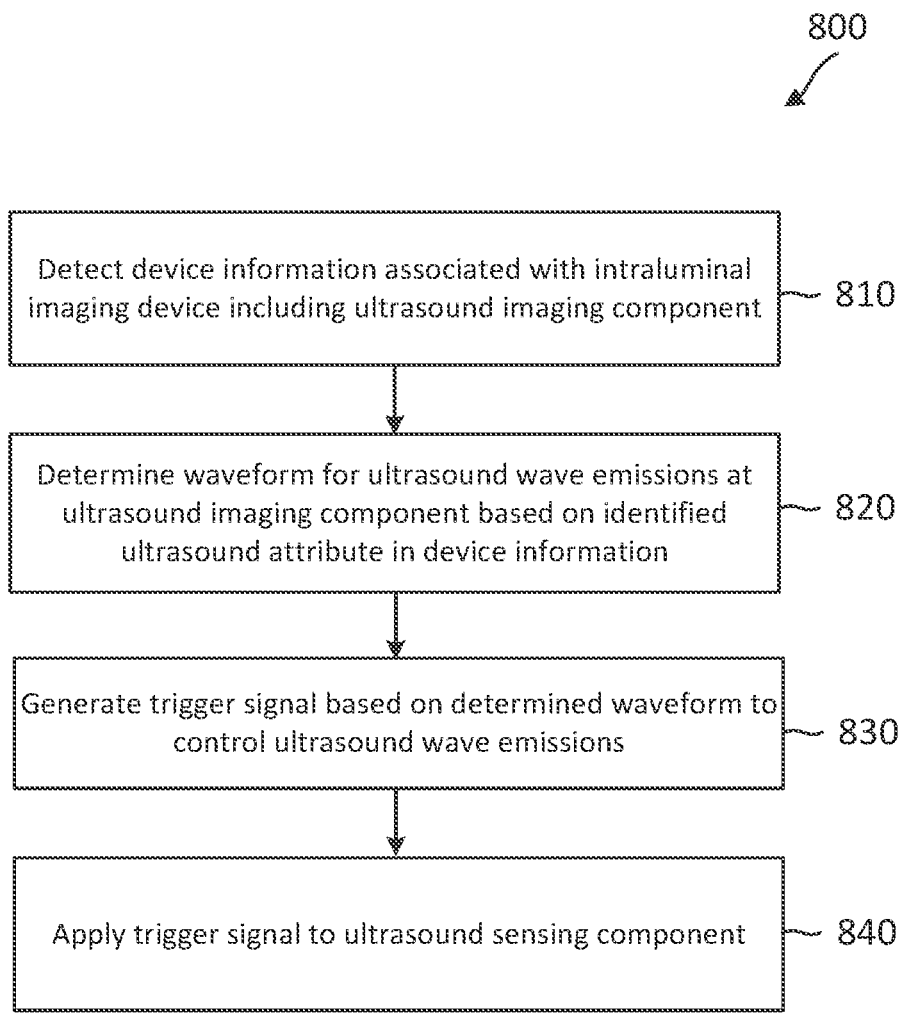
FIG. 8 is a flow diagram of a method of generating and controlling ultrasound transmit pulses, according to aspects of the disclosure.

FIG. 8 is a flow diagram of a method 800 of generating and controlling ultrasound transmit pulses, according to aspects of the disclosure. Steps of the method 800 can be executed by the system 100. The method 800 may employ similar mechanisms as in the system configurations 200, 400, and 500, the ultrasound imaging configuration 300, and the FPGA 600 implementation as described with respect to FIGS. 2, 4, 5, 3, and 6, respectively. As illustrated, the method 800 includes a number of enumerated steps, but embodiments of the method 800 may include additional steps before, after, and in between the enumerated steps. In some embodiments, one or more of the enumerated steps may be omitted or performed in a different order.

At step 810, the method 800 includes detecting, by a PIM (e.g., the PIM 104), information (e.g., the device information 212) associated with an intraluminal imaging device (e.g., the intraluminal imaging devices 102) including an ultrasound imaging component (e.g., the ultrasound imaging component 110). The intraluminal imaging device may be plugged into a connector (e.g., the device interface 202) of the PIM and in communication with the PIM. The information may identify ultrasound attributes (e.g., operational parameters for ultrasound emissions) and/or device attributes (e.g., device types, device models, serial number, device configuration parameters) associated with the intraluminal imaging device.

At step 820, the method 800 includes determining, by a processing component (e.g., the processing component 620) a waveform characteristic for ultrasound wave emissions (e.g., the ultrasound waves 302) at the ultrasound imaging component based on the detected information (e.g., the identified ultrasound attributes and/or device attributes).

At step 830, the method 800 includes generating, by a trigger signal generation component (e.g., the trigger signal generation component 220 and the FSM 650) of the PIM, a trigger signal (e.g., the trigger signals 228 and 700) based on the determined waveform characteristic to control the ultrasound wave emissions at the ultrasound imaging component.

At step 840, the method 800 includes applying, by the trigger signal generation component, the trigger signal to the ultrasound imaging component.

In some embodiments, the determining of the waveform characteristic includes determining at least one of a number of waveform pulses for the trigger signal, a periodicity of the waveform pulses, a duty cycle of the waveform pulses, a polarity of the waveform pulses, or an amplitude of the waveform pulses based on the detected information.

In some embodiments, the method 800 may further include configuring, by a sequencing component (e.g., the sequencer 224) of the PIM, one or more timing sequences (e.g., the sequence 330) for one or more of transducer elements (e.g., the transducers 310) in a transducer array of the ultrasound imaging component to produce the ultrasound wave emissions at the ultrasound imaging component.

In some embodiments, the method 800 may further include detecting, by a detection component (e.g., the detection component 222) of the PIM, an attachment of the intraluminal imaging device to the PIM. The detection may include reading the device information from the intraluminal imaging device (e.g., stored in a memory 210) upon the detection.

In some embodiments, the method 800 may further include requesting a configuration (e.g., the parameter configurations 230) for the intraluminal imaging device from a host system (e.g., the host 106) based on the detected information and receiving the configuration from the host system in response to the request. The waveform characteristic may be determined based on the received configuration.

In some embodiments, the method 800 may further include storing, at a memory (e.g., the memory 410) of the PIM, a plurality of configurations (e.g., the parameter configurations 430) associated with a plurality of different ultrasound imaging components comprising a plurality of different ultrasound attributes. The method 800 may select a configuration from the plurality of configurations based on the detected information. The waveform characteristic may be determined based on the selected configuration. In some other embodiments, the method 800 may employ a configuration received from the host and/or a configuration selected from among multiple configurations stored in the PIM to determine the waveform characteristic.

In some embodiments, the method 800 may further include receiving a request to modify a parameter (e.g., via the user inputs 510) associated with the waveform characteristic of the ultrasound wave emissions while the ultrasound imaging component is performing an imaging procedure. The method 800 may determine an updated waveform characteristic for the ultrasound wave emissions at the ultrasound imaging component based on the modified parameter. The method 800 may generate an updated trigger signal (e.g., the trigger signals 528 and 700) based on the updated waveform characteristic. The method 800 may apply the updated trigger signal to the ultrasound imaging component during the imaging procedure. In some instances, images capture by the ultrasound imaging component with the updated trigger signal can be displayed on a monitor or console (e.g., the display 108).

Aspects of the present disclosure can provide several benefits. For example, the automatic detection and identification of an intraluminal ultrasound imaging device upon attachment to the PIM 104 can allow the PIM 104 to generate suitable ultrasound transmit pulses for the attached device 102 without having to change any system hardware or restart the system. The real-time reconfiguration of the ultrasound transmit pulses can allow a user to quickly modify any ultrasound waveform parameters to generate a desired imaging views or imaging modes during a live imaging procedure without having to stop, configure, and/or restart the procedure. The extraction of the key ultrasound waveform parameters, such as ultrasound operating center frequency (e.g., via the durations 712 and 722) and pulse energy (e.g., via the levels 714) into programmable parameters can provide flexibility in waveform generations. The hardware implementation of the state machine (e.g., the FSM 650) for controlling and generating the trigger signals can provide accurate and precise response time.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging system, comprising:
    a first intraluminal imaging device comprising a first ultrasound imaging component;
    a patient interface module (PIM) configured for communication with the first intraluminal imaging device and a different, second intraluminal imaging device comprising a second ultrasound imaging component; and
    a host system separate from and configured for communication with the PIM, wherein the host system comprises a memory configured to store a first parameter configuration specific to the first ultrasound imaging component and a different, second parameter configuration specific to the second ultrasound imaging component,
    wherein, when the PIM is in communication with the first intraluminal imaging device, the PIM is configured to:
        read first device information from the first intraluminal imaging device, wherein the first device information is representative of the first ultrasound imaging component;
        provide a request to the host system, based on the first device information, to transmit the first parameter configuration from the memory to the PIM;
        receive, in response to the request, the first parameter configuration from the host system; and
        control, using the first parameter configuration, the first ultrasound imaging component to produce first ultrasound wave emissions,
    wherein, when the PIM is in communication with the second intraluminal imaging device, the PIM is configured to:
        read second device information from the second intraluminal imaging device, wherein the second device information is representative of the second ultrasound imaging component;
        provide a request to the host system, based on the second device information, to transmit the second parameter configuration from the memory to the PIM;
        receive, in response to the request, the second parameter configuration from the host system; and
        control, using the second parameter configuration, the second ultrasound imaging component to produce different, second ultrasound wave emissions.

2. The system of claim 1, further comprising the second intraluminal imaging device.

3. The system of claim 1,
    wherein, to control the first ultrasound imaging component to produce first ultrasound wave emissions, the PIM is configured to generate a first trigger signal based on the first parameter configuration,
    wherein, to control the second ultrasound imaging component to produce second ultrasound wave emissions, the PIM is configured to generate a different, second trigger signal based on the second parameter configuration.

4. The system of claim 1,
    wherein the first ultrasound wave emissions comprise a first waveform, and
    wherein the second ultrasound wave emissions comprise a different, second waveform.

5. The system of claim 1, wherein the PIM is configured to:
    detect whether the first intraluminal imaging device or the second intraluminal imaging device is attached; and
    determine whether to request the first parameter configuration or the second parameter configuration from the host system based on the detection.

6. The system of claim 1,
    wherein the first intraluminal imaging device comprises a first device memory storing the first device information,
    wherein the second intraluminal imaging device comprises a second device memory storing the second device information.

7. The system of the claim 1, wherein the host system is configured to:
    generate a first ultrasound image associated with the first ultrasound wave emissions; and
    generate a second ultrasound image associated with the second ultrasound wave emissions.

8. The system of claim 7,
    further comprising a display configured for communication with the host system,
    wherein the display is configured to:
        display the first ultrasound image; and
        display the second ultrasound image.

9. The system of claim 1,
    wherein the first parameter configuration is specific to operation of the first ultrasound imaging component to produce the first ultrasound wave emissions, and
    wherein the second parameter configuration is specific to operation of the second ultrasound imaging component to produce the second ultrasound wave emissions.

10. The system of claim 9, wherein the first parameter configuration and the second parameter configuration comprise at least one of an ultrasound center frequency, an ultrasound signal bandwidth, an ultrasound pulse duration, a number of signal zones in a pulse, a pulse amplitude, a pulse polarity, a pulse duty cycle, or a number of pulses.

11. The system of claim 1,
    wherein the first intraluminal imaging device comprises a first intravascular ultrasound (IVUS) catheter, and
    wherein the second intraluminal imaging device comprises a second IVUS catheter.

12. The system of claim 11,
    wherein the first IVUS catheter comprises an array IVUS catheter; and
    wherein the second IVUS catheter comprises a rotational IVUS catheter.

13. The system of claim 11,
    wherein the first ultrasound imaging component comprises an array of transducer elements, and
    wherein the second ultrasound imaging component comprises a single transducer element.

14. The system of claim 11,
    wherein the first IVUS catheter is configured for imaging a coronary vessel, and
    wherein the second IVUS catheter is configured for imaging a peripheral vessel.

* * * * *